(12) United States Patent
Kim et al.

(10) Patent No.: US 8,791,152 B2
(45) Date of Patent: Jul. 29, 2014

(54) STABLE PHARMACEUTICAL COMPOSITION CONTAINING DOCETAXEL AND A METHOD OF MANUFACTURING THE SAME

(75) Inventors: Nam Ho Kim, Seongnam-si (KR); Jin Young Lee, Suwon-si (KR); Jae-Sun Kim, Suwon-si (KR); Nam Kyu Lee, Suwon-si (KR); Woo Jae Jang, Gunpo-si (KR); Joon Gyo Oh, Suwon-si (KR); Yoon-Jung Lee, Yongin-si (KR); Woong Sik Kim, Suwon-si (KR); Jin-Heung Sung, Bucheon-si (KR); Key An Um, Suwon-si (KR)

(73) Assignee: SK Chemicals Co., Ltd., Gyeonggi-Do (KR)

(*) Notice: Subject to any disclaimer, the term of this patent is extended or adjusted under 35 U.S.C. 154(b) by 174 days.

(21) Appl. No.: 12/301,700

(22) PCT Filed: May 22, 2007

(86) PCT No.: PCT/KR2007/002479
§ 371 (c)(1),
(2), (4) Date: Jan. 27, 2009

(87) PCT Pub. No.: WO2007/136219
PCT Pub. Date: Nov. 29, 2007

(65) Prior Publication Data
US 2009/0163574 A1    Jun. 25, 2009

(30) Foreign Application Priority Data

May 22, 2006 (KR) .......... 10-2006-0045715
May 21, 2007 (KR) .......... 10-2007-0049340

(51) Int. Cl.
*A61K 31/335* (2006.01)

(52) U.S. Cl.
USPC .......................................... 514/449

(58) Field of Classification Search
USPC .......................................... 514/449
See application file for complete search history.

(56) References Cited

U.S. PATENT DOCUMENTS 5,472,954 A * 12/1995 Loftsson .................. 514/58
6,645,528 B1 11/2003 Straub et al.
2004/0127551 A1 7/2004 Zhang et al.

FOREIGN PATENT DOCUMENTS

| JP | 2001-522816 A | 11/2001 |
| JP | 2002-537317 A | 11/2002 |
| JP | 2003-500368 A | 1/2003 |
| JP | 2003-500438 A | 1/2003 |
| JP | 2005-075783 | 3/2005 |
| KR | 10-2000-0061113 A | 10/2000 |
| WO | WO 98/30205 A | 7/1998 |
| WO | WO 98/55148 | 12/1998 |
| WO | WO 99/24073 A | 5/1999 |
| WO | WO 03/043602 A1 | 5/2003 |

* cited by examiner

*Primary Examiner* — Paul Zarek
(74) *Attorney, Agent, or Firm* — Frommer Lawrence & Haug LLP; Ronald R Santucci

(57) ABSTRACT

The present invention relates to a stable pharmaceutical composition for injection containing docetaxel and a method of preparing the same. More particularly, the present invention relates to a pharmaceutical composition for injection containing docetaxel having better storage stability than conventional medications, which is prepared by dissolving docetaxel, a water-insoluble compound, in distilled water after mixing it with cyclodextrin (CD) and a water-soluble polymer such as hydroxypropyl methylcellulose (HPMC), polyethylene glycol (PEG) or polyvinylpyrrolidone (PVP) and lyophilizing the mixture, and a method of preparing the same.

24 Claims, No Drawings

STABLE PHARMACEUTICAL COMPOSITION CONTAINING DOCETAXEL AND A METHOD OF MANUFACTURING THE SAME

This application is a 371 of PCT/KR2007/002479 filed on May 22, 2007, published on Nov. 29, 2007 under publication number WO 2007/136219 A1 which claims priority benefits from South Korean Patent Application Number 10-2006-0045715 filed May 22, 2006, and South Korean Patent Application Number 10-2007-0049340 filed May 21, 2007, the disclosures of which are incorporated herein by reference.

TECHNICAL FIELD

The present invention relates to a stable pharmaceutical composition for injection containing docetaxel and a method of preparing the same. More particularly, the present invention relates to a pharmaceutical composition for injection containing docetaxel with improved storage stability as compared to those of conventional medications, prepared by dissolving docetaxel, a water-insoluble compound, in distilled water after mixing it with cyclodextrin (CD) and a water-soluble polymer such as hydroxypropyl methylcellulose (HPMC), polyethylene glycol (PEG) or polyvinylpyrrolidone (PVP) and lyophilizing the mixture, and a method of preparing the same.

BACKGROUND ART

Docetaxel is an anti-cancer agent effective in treating non-small cell lung, breast, ovarian, head and cervical cancers. It is commercially available under Taxotere® by Sanofi-Aventis. Docetaxel is a highly lipophilic semisynthetic taxoid but is almost insoluble in water. Docetaxel is currently distributed in a blister carton package consisting of one single-dose Taxotere containing docetaxel dissolved in polysorbate 80 vial and one single-dose solvent for Taxotere containing 13% (w/w) ethanol vial, wherein the above two are mixed together to prepare a premix with a solubility of 10 mg/mL and then added into an infusion bag containing physiological saline solution. The final infusion solution should have a docetaxel concentration ranging from 0.3 to 0.9 mg/mL. If the concentration is higher than 0.9 mg/mL, there may appear precipitation. In addition, hypersensitive reaction may occur due to the use of polysorbate 80 and the presence of ethanol may incur side reactions.

WO 98/30205 discloses a method of using PEGylated vitamin E as a surfactant and US 2004/0127551 discloses a method of using vitamin E TPGS (D-α-tocopheryl polyethylene glycol 1000 succinate). But, they failed to obtain a stable composition containing a high concentration of docetaxel.

Korean Patent No. 310839 discloses a method of preparing a polyvinylpyrrolidone matrix and mixing it with anhydrous ethanol and a solvent such as polyoxyethylene glycerol ricinoleate, polysorbate 80, anhydrous ethanol and polyethylene glycol to obtain an injection. However, the above invention is also not advantageous in that the substances that may induce alcoholism or hypersensitive reaction (ethanol and polysorbate 80) are included.

WO 99/24073 filed in 1997 discloses a method to increase the solubility of docetaxel in water by using cyclodextrin instead of a surfactant. More particularly, docetaxel is dissolved in a small amount of ethanol and the resultant solution is added to a 5% dextrose solution of acetyl-γ-cyclodextrin (Ac-γ-CD) or hydroxypropylmethyl-β-cyclodextrin (HP-β-CD). Then, ethanol is removed as much as possible by evaporation or other method as appropriate. Subsequently, lyophilization is performed to obtain a wanted lyophilized composition. A suitable mixed ratio of docetaxel to cyclodextrin is from 1:25 to 1:400 based on weight. An injection obtained by further diluting the resultant lyophilized composition in a 5% dextrose solution has a concentration of 0.3-1.2 mg/mL and enables to maintain physical stability for over 72 hours.

However, this invention also has the problem that the ethanol used to dissolve docetaxel may not be eliminated, and precipitation may occur if the resultant liquid composition has a low docetaxel concentration. Further, since lyophilization is performed after adjusting the docetaxel concentration of the liquid composition to 0.5-1.25 mg/mL, the dried substance has a large volume, leading to a smaller throughput for a single batch of the same lyophilizer. Besides, when the resultant lyophilized composition is dissolved or diluted for use, its physical stability tends to decrease and the resultant lyophilized composition does not have the solubility 10 mg/mL, which is the solubility of the Taxotere's pre-mix solution. In case an injection for clinical administration is prepared as disclosed in the patent by dissolving it to a docetaxel concentration of 0.5-1.25 mg/mL using 5% dextrose or 0.9% saline solution, about 150-200 mg of the substance should be used considering the clinical dose of 100 mg/m². Consequently, about 150-200 mL of diluent is required and it is very difficult to prepare the required injection.

Accordingly, there is still a need for the development of a new pharmaceutical preparation that can offer improved storage stability and solubility as compared to those of conventional formulation and does not require a harmful solubilizing agent such as polysorbate or ethanol.

DISCLOSURE OF THE INVENTION

Technical Problem

The present inventors completed the present invention by developing a pharmaceutical composition for injection containing docetaxel with improved solubility and stability as compared to those of conventional agents by combining water-insoluble docetaxel with hydroxypropyl-β-cyclodextrin and a water-soluble polymer such as hydroxypropyl methylcellulose (HPMC), polyethylene glycol (PEG) or polyvinylpyrrolidone (PVP) in distilled water to improve the stability of docetaxel in an aqueous solution.

Accordingly, an object of the present invention is to provide a stable pharmaceutical composition for injection containing docetaxel and a method of preparing the same.

Technical Solution

The present invention relates to a pharmaceutical composition for injection containing docetaxel with superior storage stability comprising docetaxel, cyclodextrin and a water-soluble polymer such as hydroxypropyl methylcellulose (HPMC), polyethylene glycol (PEG) or polyvinylpyrrolidone (PVP).

The present invention also relates to a method of preparing a pharmaceutical composition for injection containing docetaxel with superior storage stability, comprising:

1) mixing and dissolving docetaxel with cyclodextrin and a water-soluble polymer selected from hydroxypropyl methylcellulose (HPMC), polyethylene glycol (PEG) or polyvinylpyrrolidone (PVP) in distilled water;

2) sterilizing and lyophilizing the resultant mixture to obtain a lyophilized composition; and 3) diluting the lyophilized composition in distilled water, dextrose solution or a physiological saline solution.

Hereunder is given a detailed description of the present invention.

The present invention relates to preparation of a stable pharmaceutical composition for injection comprising docetaxel in high concentration by dissolving docetaxel in distilled water containing a water-soluble polymer selected from hydroxypropyl methylcellulose (HPMC), polyethylene glycol (PEG) or polyvinylpyrrolidone (PVP) without using additive caused adverse effect such as ethanol or polysorbate.

The process of preparing a pharmaceutical composition for injection containing docetaxel in accordance with the present invention is described in detail herein below.

In step 1, docetaxel is mixed with cyclodextrin and a water-soluble polymer in distilled water. Preferably, the docetaxel used in the present invention is in an anhydrous form or a hydrate form.

Cyclodextrins have a hydrophobic cavity of regular size and protect hydrophobic compounds from external environment by lodging them in the cavity. Typically, cyclodextrins are classified into α-cyclodextrin, β-cyclodextrin and γ-cyclodextrin depending on the property and size. Other than the aforementioned three kinds, other cyclodextrin derivatives may be used in the present invention. Preferably, β-cyclodextrins having a cavity diameter ranging from 6.0 to 6.5 Å or derivatives thereof are used. More preferably, hydroxypropyl-β-cyclodextrin (HPBCD), which is commercially available as injection and listed in European Pharmacopeia, is used. Preferably, cyclodextrin is used 5-400 parts by weight, more preferably 50-100 parts by weight, per 1 part by weight of docetaxel. If cyclodextrin is used excessively, the liquid composition becomes so viscous that it cannot pass through 0.22 μm filter paper well. If cyclodextrin is used too little, it is impossible to attain suitable solubility and stability. For the hydroxypropyl-β-cyclodextrin (HPBCD), one having a degree of molecular substitution (MS) of 0.2-1.0, more preferably 0.4-0.8, is adequate. If the degree of molecular substitution is too low, solubility will be poor. In contrast, if it is too high, the composition becomes too viscous, thus making the handling difficult.

The water-soluble polymer is used in the present invention to improve solubility and stability in the solution and increase solubility of cyclodextrin. Typically, polyethylene glycol (PEG), polyvinylpyrrolidone (PVP), carboxymethyl cellulose (CMC), hydroxypropyl cellulose (HPC), hydroxymethyl cellulose (HMC), hydroxyethyl cellulose (HEC), hydroxypropyl methylcellulose (HPMC), hydroxypropylethyl cellulose (HPEC), etc., is used for the purpose. Preferably, hydroxypropyl methylcellulose (HPMC), polyethylene glycol (PEG) or polyvinylpyrrolidone (PVP) is used in the present invention. For hydroxypropyl methylcellulose (HPMC), one having a viscosity of 5-100,000 cps is preferable, more preferably one having a viscosity of 100-4,000 cps. If the viscosity of hydroxypropyl methylcellulose (HPMC) is too low, its solubility and stability will decrease significantly. In contrast, if the viscosity is too high, handling and preparation into an injection become difficult. For polyethylene glycol (PEG), there are many products having an average molecular weight ranging from 300 to 150,000 available. Preferably, one having an average molecular weight ranging from 300 to 600 is used for injection. Particularly, the products, which are permitted to be used, having an average molecular weight of 300, 400 and 600, are used. And, for polyvinylpyrrolidone, one having a K-value ranging from 10 to 20 is preferable. If the K-value of polyvinylpyrrolidone is smaller than 10, its solubility and stability will decrease significantly and, if it exceeds 20, handling and preparation into an injection will become difficult.

The water-soluble polymer is preferably comprised in 0.1-100 parts by weight, more preferably in 1.0-10.0 parts by weight, per 1 part by weight of docetaxel. If the water-soluble polymer is used in less than 1.0 part by weight, improvement of solubility and stability is minimal. In contrast, if it is used in excess of 10.0 parts by weight, the composition becomes too viscous, making filtering and washing difficult.

The water for injection used in the present invention may be any one that can be used as injection. Preferably, distilled water for injection is used.

The resultant solution is prepared into a docetaxel concentration of 1.5-20 mg/mL. If the concentration is lower than 1.5 mg/mL, the throughput of a single batch of the same lyophilizer decreases, resulting in the increase of production cost. In contrast, if the concentration is higher than 20 mg/mL, the viscosity increases without further improvement of the solubility of docetaxel, making the following sterilization process complicated.

In step 2, the mixture solution is heated and stirred for stabilization and freeze-dried after sterilization to prepare a lyophilized composition. The stirring is performed in the temperature range of 5-50° C., preferably 15-30° C. The resultant mixture solution is frozen at low temperature and the pressure is lowered at −50 to −80° C. for lyophilization. The resultant lyophilized composition has white to pale yellow color.

The resultant lyophilized composition has outstanding stability against temperature and humidity. Thus, it can be stored for a long period of time, easily prepared into injection and can endure the temperature and humidity of the production processes without being decomposed.

Further, because ethanol or other additives that may cause hypersensitive reactions are not present, the composition is not harmful to the human body at all.

In step 3, the lyophilized composition is diluted. The diluent may be any solution that can be used in injections, and preferably, water for injection, dextrose solution or a physiological saline solution for injection. The dilution is performed in two stages. At the first stage, the lyophilized composition is diluted with a variety of diluents prior to being prepared into the final injection. An adequate dilution concentration of docetaxel is 2-20.0 mg/mL, more preferably 2.5-10 mg/mL. If the concentration is lower than 2 mg/mL, a large-sized vial has to be used, which increases cost and makes handling difficult. If the concentration is higher than 20.0 mg/mL, the solution becomes too viscous, making the subsequent dilution difficult. At the second stage, the lyophilized composition is prepared into a clinically available concentration of 0.2-2.0 mg/mL. The lyophilized composition is diluted in a vial again with the diluent used in the first stage. If the concentration is lower than 0.2 mg/mL, a large amount should be injected to a patient.

Advantageous Effects

Since the liquid composition and lyophilized composition containing docetaxel according to the present invention has excellent stability, it can be stored for a considerably long period of time, easily prepared into injection and also can endure the temperature and humidity of the production processes without being decomposed. Further, due to the absence of ethanol or polysorbate, the compositions are not harmful to humans.

MODE FOR CARRYING OUT THE INVENTION

Practical and presently preferred embodiments of the present invention are illustrated as shown in the following examples. However, it will be appreciated that those skilled in the art may, in consideration of this disclosure, make modifications and improvement within the spirit and scope of the present invention.

Examples 1 to 12

32 mg of docetaxel trihydrate, hydroxypropyl methylcellulose (HPMC) or polyvinylpyrrolidone (PVP) and hydroxypropyl-β-cyclodextrin (HPBCD) were weighed and dissolved in distilled water for injection at room temperature as shown in Table 1. The solution was filtered through 0.22 μm filter paper and sterilized. After solubility measurement, the filtrate was frozen around −40° C. and freeze-dried to obtain a lyophilized composition. Solubility was measured by liquid chromatography using a UV detector (230 nm).

TABLE 1

| Classification | | Example 1 | Example 2 | Example 3 | Example 4 | Example 5 | Example 6 |
|---|---|---|---|---|---|---|---|
| Docetaxel trihydrate (mg) | | 96 | 96 | 96 | 96 | 96 | 96 |
| HPBCD (mg) | M = 0.6 | 4500 | — | 9000 | — | 6300 | — |
| | M = 1.0 | — | 4500 | — | 9000 | — | 6300 |
| HPMC (mg) | 5 cps | 90 | 450 | — | — | 90 | — |
| | 100 cps | — | — | 90 | 360 | — | 450 |
| Distilled water for injection (mL) | | 18 | 18 | 9 | 9 | 24 | 24 |
| Solubility (mg/mL) | | 3.9 | 3.8 | 5.2 | 5.1 | 3.0 | 3.1 |

| Classification | | Example 7 | Example 8 | Example 9 | Example 10 | Example 11 | Example 12 |
|---|---|---|---|---|---|---|---|
| Docetaxel trihydrate (mg) | | 96 | 96 | 96 | 96 | 96 | 96 |
| HPBCD (mg) | M = 0.6 | 4500 | — | 9000 | — | 6300 | — |
| | M = 1.0 | — | 4500 | — | 9000 | — | 6300 |
| HPMC (mg) | 5 cps | 90 | 450 | — | — | 90 | — |
| | 100 cps | — | — | 90 | 360 | — | 450 |
| Distilled water for injection (mL) | | 9 | 9 | 9 | 9 | 9 | 9 |
| Solubility (mg/mL) | | 6.6 | 6.8 | 5.3 | 5.2 | 5.4 | 5.5 |

Examples 13 to 24

30 mg of anhydrous docetaxel, polyvinylpyrrolidone (PVP), HPMC or polyethylene glycol (PEG) and hydroxypropyl-β-cyclodextrin (HPBCD) were weighed and dissolved in distilled water for injection at room temperature as shown in Table 2. The solution was filtered through 0.22 μm filter paper and sterilized. After solubility measurement, the filtrate was frozen around −40° C. and freeze-dried to obtain a lyophilized composition. Its solubility was measured by liquid chromatography using a UV detector (230 nm).

TABLE 2

| Classification | | Example 13 | Example 14 | Example 15 | Example 16 | Example 17 | Example 18 |
|---|---|---|---|---|---|---|---|
| Docetaxel anhydrous (mg) | | 90 | 90 | 135 | 135 | 90 | 90 |
| HPBCD (mg) | M = 0.6 | 4500 | — | 9000 | — | 6300 | — |
| | M = 1.0 | — | 4500 | — | 9000 | — | 6300 |
| PEG (mg) | MW 400 | 90 | 450 | — | — | 270 | — |
| HPMC (mg) | 100 cps | — | — | 135 | 360 | — | 360 |
| Distilled water for injection (mL) | | 30 | 30 | 6 | 6 | 12 | 12 |
| Solubility (mg/mL) | | 2.6 | 2.7 | 8.9 | 9.2 | 4.9 | 5.0 |

| Classification | | Example 19 | Example 20 | Example 21 | Example 22 | Example 23 | Example 24 |
|---|---|---|---|---|---|---|---|
| Docetaxel anhydrous (mg) | | 90 | 90 | 135 | 135 | 90 | 90 |
| HPBCD (mg) | M = 0.6 | — | 4500 | 9000 | — | 6300 | — |
| | M = 1.0 | 4500 | — | — | 9000 | — | 6300 |
| PVP (mg) | K-12 | 90 | 450 | — | — | 270 | — |
| | K-17 | — | — | 45 | 120 | — | 360 |
| Distilled water for injection (mL) | | 6 | 6 | 6 | 6 | 12 | 12 |
| Solubility (mg/mL) | | 8.6 | 8.7 | 9.0 | 9.2 | 5.0 | 4.9 |

Comparative Example 1

A white lyophilized composition was prepared same as in Example 19, except for not using a water-soluble polymer.

Comparative Example 2

A lyophilized composition was prepared using docetaxel and HPBCD as in Example 1.10 of WO 99/24073. 60 mg of docetaxel was dissolved in 3 mL of ethanol and 3000 mg of HPBCD was added. 60 mL of purified water for injection was added to the mixture. The concentration of the resultant transparent solution was adjusted to 1 mg/mL. The resultant solution was frozen rapidly in dry ice and freeze-dried to obtain a lyophilized composition in powder form. The docetaxel content of the powder was 2% w/w.

Comparative Example 3

A lyophilized composition was prepared according to the method disclosed in Korean Patent No. 0136722. 96 mg of docetaxel trihydrate was dissolved in 1020 μL of anhydrous ethanol and 2490 mg of polysorbate 80 was added. Ethanol was evaporated under reduced pressure at 30° C. for 2 hours in a rotary evaporator.

Experimental Example 1

Stability Test (Liquid State)

The lyophilized compositions prepared in Examples 1-24 and Comparative Examples 1 and 3 were made into a solution by adding distilled water for injection. Stability change at room temperature was monitored by measuring concentration with HPLC.

TABLE 3

| Classification | Initial concentration (mg/mL) | Concentration, 48 hours later (mg/mL) | Concentration, 96 hours later (mg/mL) | Solution state, 96 hours later |
|---|---|---|---|---|
| Example 1 | 3.8 | 3.8 | 3.8 | Clear solution |
| Example 3 | 5.1 | 5.1 | 5.0 | Clear solution |
| Example 5 | 3.1 | 3.0 | 3.0 | Clear solution |
| Example 7 | 6.7 | 6.6 | 6.5 | Clear solution |
| Example 9 | 5.3 | 5.3 | 5.3 | Clear solution |
| Example 11 | 5.3 | 5.3 | 5.2 | Clear solution |
| Example 14 | 2.8 | 2.8 | 2.6 | Clear solution |
| Example 16 | 9.1 | 9.1 | 9.1 | Clear solution |
| Example 18 | 5.0 | 5.0 | 4.9 | Clear solution |
| Example 20 | 8.8 | 8.7 | 8.6 | Clear solution |
| Example 22 | 9.3 | 9.2 | 9.1 | Clear solution |
| Example 24 | 4.8 | 4.8 | 4.7 | Clear solution |
| Comparative Example 1 | 8.6 | 5.2 | 1.9 | Precipitation |

The lyophilized compositions prepared in Example 24 and Comparative Example 3 were dissolved in 0.9% saline solution and diluted to 2.0 mg/mL and tested.

TABLE 4

| Classification | Initial concentration (mg/mL) | Concentration, 10 hours later (mg/mL) | Concentration, 36 hours later (mg/mL) | Solution state, 36 hours later |
|---|---|---|---|---|
| Comparative Example 3 | 2.0 | 1.8 | 1.2 | Precipitation |
| Example 24, diluted | 1.9 | 1.9 | 1.8 | Clear solution |

As shown in Table 3, the lyophilized compositions in accordance with the present invention (Examples 1-24) showed better storage stability than that of Comparative Example 1. Further, the lyophilized compositions in accordance with the present invention showed a better stability even in diluted state than that of Comparative Example 3, as shown in Table 4.

Experimental Example 2

Stability Test (Dry State)

Stability of the lyophilized compositions prepared in Examples 13 and 23 and Comparative Examples 2 and 3 was monitored while keeping them under refrigeration condition (4° C.), long-term storage condition (25° C., 60% RH) and accelerated conditions (40° C., 75% RH; 50° C., 60% RH). Stability was evaluated based on the total amount of impurities. As shown in Table 5, the lyophilized compositions of the present invention showed better stability than those of Comparative Examples 2 and 3.

TABLE 5

| Classification | | Initial | 2 weeks | 4 weeks |
|---|---|---|---|---|
| Example 13 | 4° C. | 0.13 | 0.17 | 0.31 |
| | 25° C., 60% RH | 0.13 | 0.33 | 0.41 |
| | 40° C., 75% RH | 0.13 | 0.71 | 1.74 |
| | 50° C., 60% RH | 0.13 | 1.21 | 3.30 |
| Example 23 | 4° C. | 0.09 | 0.13 | 0.16 |
| | 25° C., 60% RH | 0.09 | 0.17 | 0.20 |
| | 40° C., 75% RH | 0.09 | 0.35 | 0.30 |
| | 50° C., 60% RH | 0.09 | 0.43 | 0.53 |
| Comparative Example 2 | 4° C. | 0.32 | 0.48 | 0.49 |
| | 25° C., 60% RH | 0.32 | 0.79 | 0.82 |
| | 40° C., 75% RH | 0.32 | 2.02 | 3.21 |
| | 50° C., 60% RH | 0.32 | 3.48 | 4.12 |
| Comparative Example 3 | 4° C. | 1.84 | 2.09 | 2.66 |
| | 25° C., 60% RH | 1.84 | 4.67 | 5.43 |
| | 40° C., 75% RH | 1.84 | 8.82 | 9.31 |
| | 50° C., 60% RH | 1.84 | 15.28 | 15.74 |

Although the preferred embodiments of the present invention have been disclosed for illustrative purposes, those skilled in the art will appreciate that various modifications, additions and substitutions are possible, without departing from the scope and spirit of the present invention as disclosed in the accompanying claims.

The invention claimed is:

1. A method of preparing a stable lyophilized pharmaceutical composition containing docetaxel comprising mixing distilled water, docetaxel, cyclodextrin, and a water-soluble polymer selected from the group consisting of hydroxypropylmethyl cellulose (HPMC), polyethylene glycol (PEG) and polyvinylpyrrolidone (PVP) and lyophilizing the resultant mixture to obtain the composition, wherein the resultant mixture does not contain ethanol.

2. The method according to claim 1, wherein the docetaxel is in an anhydrous form or trihydrate form.

3. The method according to claim 1, wherein the cyclodextrin is contained 5-400 parts by weight per 1 part by weight of docetaxel.

4. The method according to claim 1, wherein the water-soluble polymer is contained 0.1-100 parts by weight per 1 part by weight of docetaxel.

5. The method according to claim 1, wherein the cyclodextrin is an α-cyclodextrin, a β-cyclodextrin or a γ-cyclodextrin.

6. The method according to claim 1, wherein the cyclodextrin is hydroxypropyl-β-cyclodextrin.

7. The method according to claim 6, wherein the hydroxypropyl-β-cyclodextrin has a degree of molecular substitution (MS) from 0.2 to 1.0.

8. The method according to claim 1, wherein the hydroxypropyl methylcellulose (HPMC) has a viscosity ranging from 5 to 100,000 cps.

9. The method according to claim 1, wherein the polyethylene glycol (PEG) has an average molecular weight ranging from 300 to 600.

10. The method according to claim 1, wherein the polyvinylpyrrolidone has a K-value ranging from 10 to 20.

11. A method of preparing the stable pharmaceutical composition for injection containing docetaxel, comprising:
  1) mixing docetaxel with cyclodextrin and a water-soluble polymer selected from hydroxypropyl methylcellulose (HPMC), polyethylene glycol (PEG) and polyvinylpyrrolidone (PVP) in distilled water;
  2) sterilizing and lyophilizing the resultant mixture to prepare a lyophilized composition; and
  3) diluting the lyophilized composition with distilled water, dextrose solution or a physiological saline solution, wherein the resultant mixture does not contain ethanol.

12. The method of claim 7, wherein the docetaxel is in an anhydrous form.

13. The method of claim 7, wherein the docetaxel is in trihydrate form.

14. The method of claim 12, wherein the hydroxypropyl methylcellulose (HPMC) has a viscosity ranging from 5 to 100,000 cps.

15. The method according to claim 12, wherein the polyethylene glycol (PEG) has an average molecular weight ranging from 300 to 600.

16. The method according to claim 12, wherein the polyvinylpyrrolidone has a K-value ranging from 10 to 20.

17. The method of claim 13, wherein the hydroxypropyl methylcellulose (HPMC) has a viscosity ranging from 5 to 100,000 cps.

18. The method according to claim 13, wherein the polyethylene glycol (PEG) has an average molecular weight ranging from 300 to 600.

19. The method according to claim 13, wherein the polyvinylpyrrolidone has a K-value ranging from 10 to 20.

20. The method according to claim 2, wherein:
  the docetaxel is in an anhydrous form or trihydrate form;
  the water-soluble polymer is contained 50-100 parts by weight per 1 part by weight of docetaxel;
  the cyclodextrin is hydroxypropyl-β-cyclodextrin and has a degree of molecular substitution (MS) from 0.2 to 1.0;
  the hydroxypropyl methylcellulose (HPMC) has a viscosity ranging from 5 to 100,000 cps;
  the polyethylene glycol (PEG) has an average molecular weight ranging from 300 to 600; and
  the polyvinylpyrrolidone has a K-value ranging from 10 to 20.

21. The method of claim 1, wherein the amount of distilled water added results in a docetaxel concentration of 1.5-20 mg/mL.

22. The method of claim 20, wherein the amount of distilled water added results in a docetaxel concentration of 1.5-20 mg/mL.

23. The method of claim 1, wherein the resultant mixture consists of distilled water, docetaxel, cyclodextrin, and a water-soluble polymer selected from the group consisting of hydroxypropylmethyl cellulose (HPMC), polyethylene glycol (PEG) and polyvinylpyrrolidone (PVP).

24. The method of claim 11, wherein the resultant mixture consists of distilled water, docetaxel, cyclodextrin, and a water-soluble polymer selected from the group consisting of hydroxypropylmethyl cellulose (HPMC), polyethylene glycol (PEG) and polyvinylpyrrolidone (PVP).

* * * * *